(12) United States Patent
Higuchi

(10) Patent No.: US 7,189,369 B2
(45) Date of Patent: Mar. 13, 2007

(54) DISTRIBUTION APPARATUS AND METHOD FOR DETACHING DISTRIBUTION TIP IN DISTRIBUTION APPARATUS

(75) Inventor: Akira Higuchi, Fukuoka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 722 days.

(21) Appl. No.: 10/658,412

(22) Filed: Sep. 10, 2003

(65) Prior Publication Data
US 2004/0067170 A1    Apr. 8, 2004

(30) Foreign Application Priority Data
Oct. 3, 2002    (JP) ............... 2002-290922

(51) Int. Cl.
  *B01L 3/02*    (2006.01)
  *G01N 1/10*    (2006.01)
(52) U.S. Cl. ............. 422/100; 436/180; 73/863.25
(58) Field of Classification Search ......... 422/99, 422/100; 436/180; 73/863.25, 864.14
  See application file for complete search history.

(56) References Cited

U.S. PATENT DOCUMENTS

| | | | | |
|---|---|---|---|---|
| 5,061,449 A | * | 10/1991 | Torti et al. | 422/100 |
| 5,736,105 A | * | 4/1998 | Astle | 422/100 |
| 5,827,745 A | * | 10/1998 | Astle | 436/54 |
| 6,182,719 B1 | * | 2/2001 | Yahiro | 141/130 |
| 6,238,626 B1 | | 5/2001 | Higuchi et al. | |
| 6,299,840 B1 | | 10/2001 | Watanabe et al. | |
| 6,358,470 B1 | * | 3/2002 | Higuchi | 422/63 |
| 6,589,483 B1 | * | 7/2003 | Maeda | 422/100 |
| 6,793,891 B2 | * | 9/2004 | Yiu | 422/100 |
| 6,810,757 B2 | * | 11/2004 | Carl | 73/864.14 |
| 7,105,129 B2 | * | 9/2006 | Ruddock | 422/63 |
| 2002/0104389 A1 | * | 8/2002 | Hovey | 73/864.17 |
| 2003/0017604 A1 | * | 1/2003 | Hitch et al. | 436/43 |
| 2004/0033554 A1 | * | 2/2004 | Powers | 435/29 |
| 2004/0096360 A1 | * | 5/2004 | Toi et al. | 422/63 |

FOREIGN PATENT DOCUMENTS

JP    11-14631    1/1999

* cited by examiner

Primary Examiner—Brian R. Gordon
(74) Attorney, Agent, or Firm—Wenderoth, Lind & Ponack, L.L.P.

(57) ABSTRACT

In the distribution apparatus and the method for detaching distribution tips of the present invention, the detaching plate provided with openings being larger in diameter than outer diameter of the nozzle and smaller in diameter than outer diameter of the distribution tip which are disposed in accordance with the arrangement of the nozzles is held to the distributing head with the nozzles set through the openings, and with the stopping portion of the detaching plate stopped by the stop portion of the stop member disposed at the tip detaching stage, the distributing head and the stop member are relatively moved in a direction of vertically moving apart, and thereby, the distribution tips are detached from the bottom ends of the nozzles. In this way, the distribution tip detaching operation can be automatically performed by a simple mechanism.

6 Claims, 15 Drawing Sheets

DISTRIBUTION APPARATUS AND METHOD FOR DETACHING DISTRIBUTION TIP IN DISTRIBUTION APPARATUS

FIELD OF THE INVENTION

The present invention relates to a distribution apparatus used for distributing a liquid sample in the field of biochemistry and the like, and to a method for detaching distribution tip in the distribution apparatus.

BACKGROUND OF THE INVENTION

In a test or analysis executed in the field of biochemistry and the like, a liquid such as test substance or reagent is distributed for subdivision onto a micro-plate that is a sample container. The distributing is executed by sucking and discharging the liquid by nozzles, and disposable distribution tips are usually installed as the nozzles.

The distribution tips are replaced each time the kind of the liquid to be distributed is changed, and the distribution tips are very frequently replaced during the test operation. Conventionally, the replacement is often manually performed, pulling out the distribution tips by hand. Also, as in the case of a distribution apparatus disclosed in Japanese Laid-open Patent H11-14631, a distributing head itself is furnished with a chip removing mechanism. However, when the replacement is performed by hand, it puts a great deal of labor on the operator because the work is very frequently performed, and in the case of providing the distributing head with a chip removing mechanism, there arises a problem such that the distributing head becomes increased in size and very complicated, causing hindrance to the realization of a compact distribution apparatus.

SUMMARY OF THE INVENTION

A distribution apparatus which sucks in a liquid by distribution tips detachably fitted to the bottom ends of nozzles disposed on a distributing head and discharges the liquid into a container, comprising:

a detaching plate having a stopping portion and provided with openings being larger in diameter than outer diameter of the nozzle and smaller in diameter than outer diameter of the distribution tip which are disposed in accordance with the arrangement of the nozzles;

a holding means which serves to make the distributing head hold the detaching plate with the nozzles set through the openings;

a tip detaching stage provided with a stop member having a stop portion to stop the stopping portion; and a distribution tip detaching means for detaching the distribution tips from the nozzles by means of the detaching plate by moving the stop member and the distributing head relatively in a direction of vertically moving apart with the stopping portion stopped by the stop portion.

A method for detaching distribution tips in a distribution apparatus, which is a method for detaching distribution tips in a distribution apparatus wherein distribution tips fitted in nozzles are detached from the nozzles in a distribution apparatus which sucks in a liquid by distribution tips detachably fitted to the bottom ends of the nozzles disposed on a distributing head, wherein a detaching plate provided with openings being larger in diameter than outer diameter of the nozzle and smaller in diameter than outer diameter of the distribution tip which are disposed in accordance with the arrangement of the nozzles is held to the distributing head with the nozzles set through the openings, and with the stopping portion of the detaching plate stopped by the stop portion of a stop member disposed at the tip detaching stage, the distributing head and the stop member are relatively moved in a direction of vertically moving apart, and thereby, the distribution tips are detached from the bottom ends of the nozzles.

DETAILED DESCRIPTION OF THE EXEMPLARY EMBODIMENTS

The present invention is intended to provide a distribution apparatus and a method for detaching distribution tips wherein the distribution tips can be automatically detached by a simple mechanism.

Exemplary Embodiment 1

Figure 1:
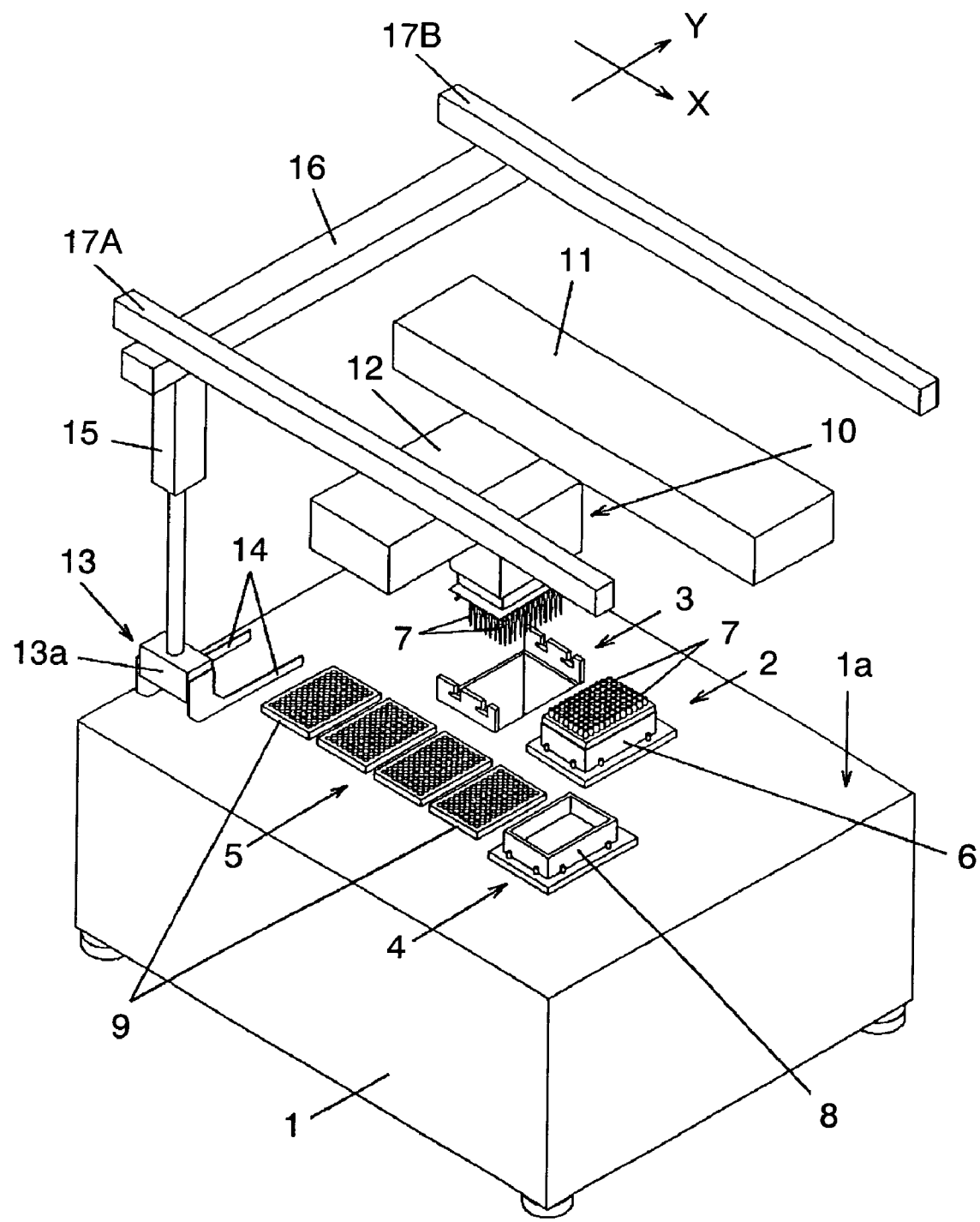
FIG. 1 is a perspective view of a distribution apparatus in the exemplary embodiment 1 of the present invention.
Figure 2:
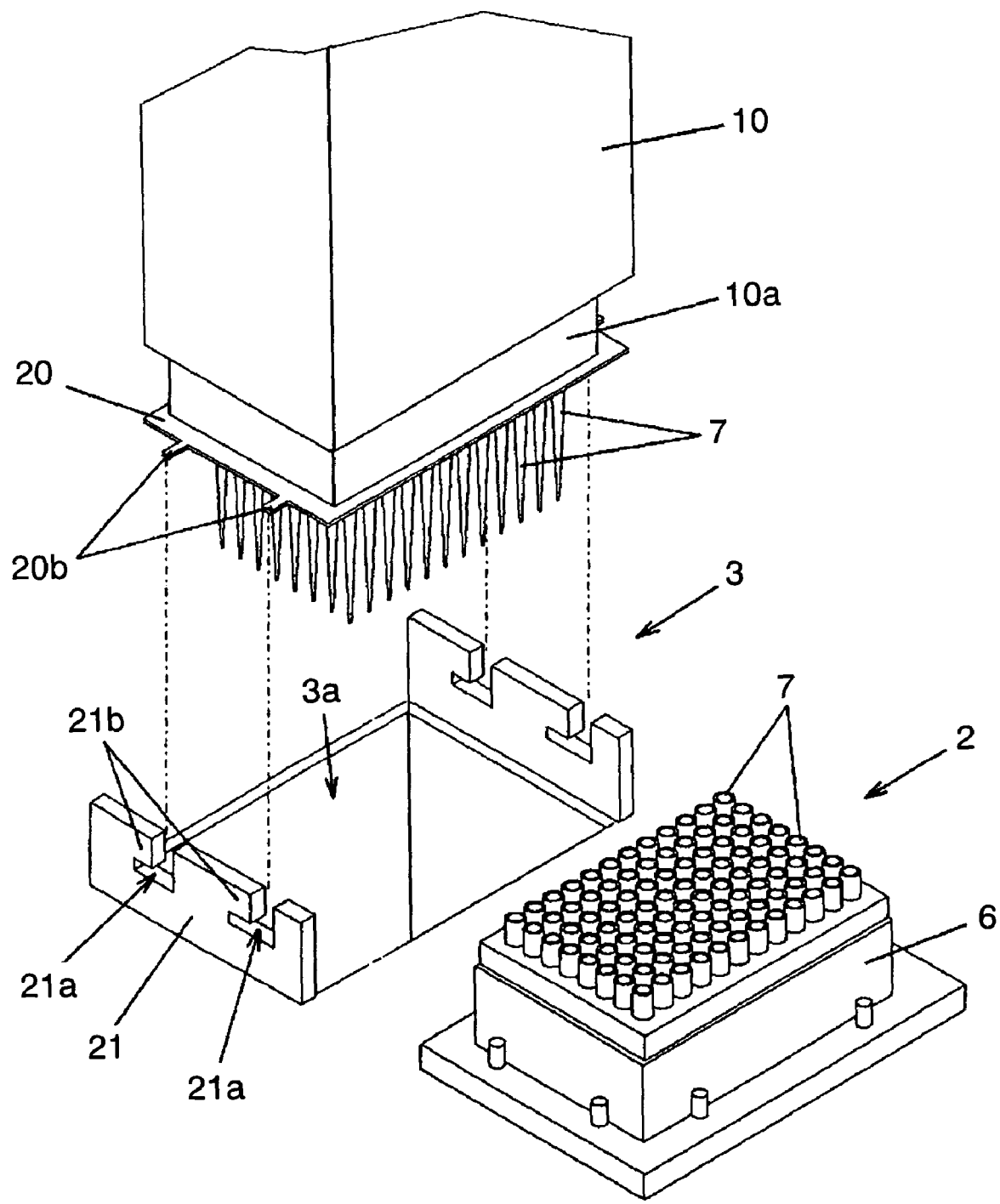
FIG. 2 is a partly perspective view of the distribution apparatus in the exemplary embodiment 1 of the present invention.
Figure 3:
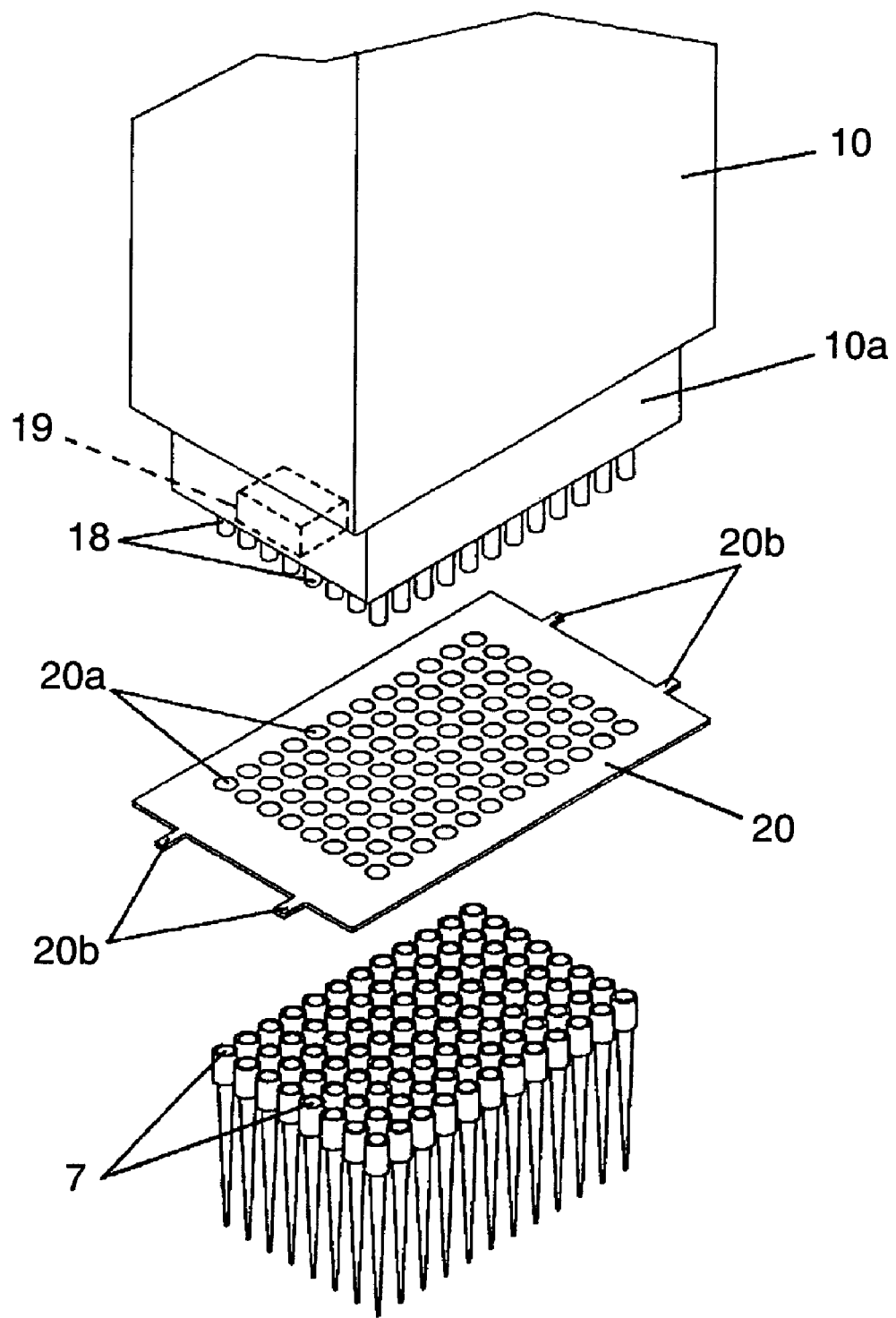
FIG. 3 is a partly perspective view of a distributing head of the distribution apparatus in the exemplary embodiment 1 of the present invention.
Figure 4:
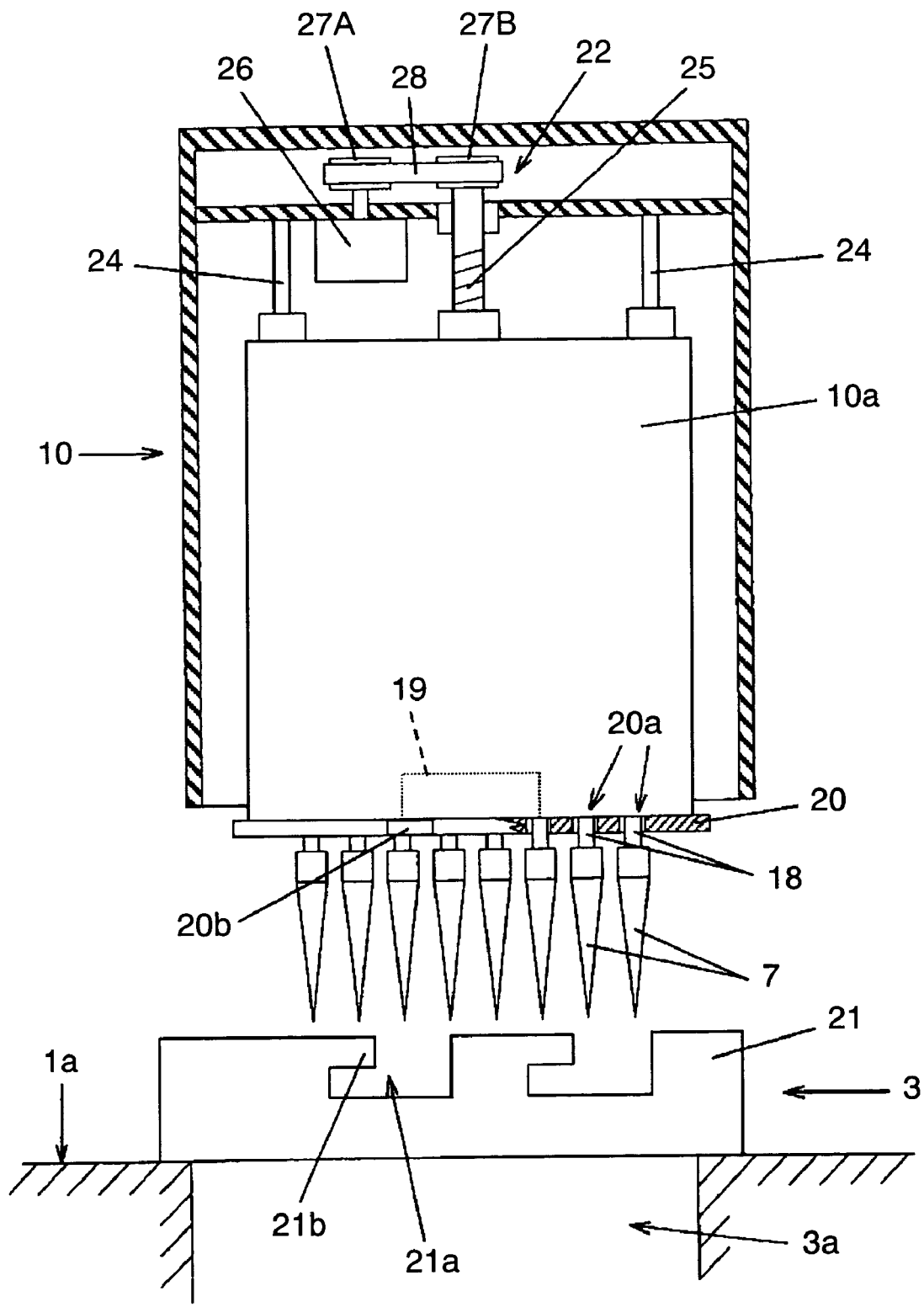
FIG. 4 is a sectional view of the distributing head of the distribution apparatus in the exemplary embodiment 1 of the present invention.
Figure 5:
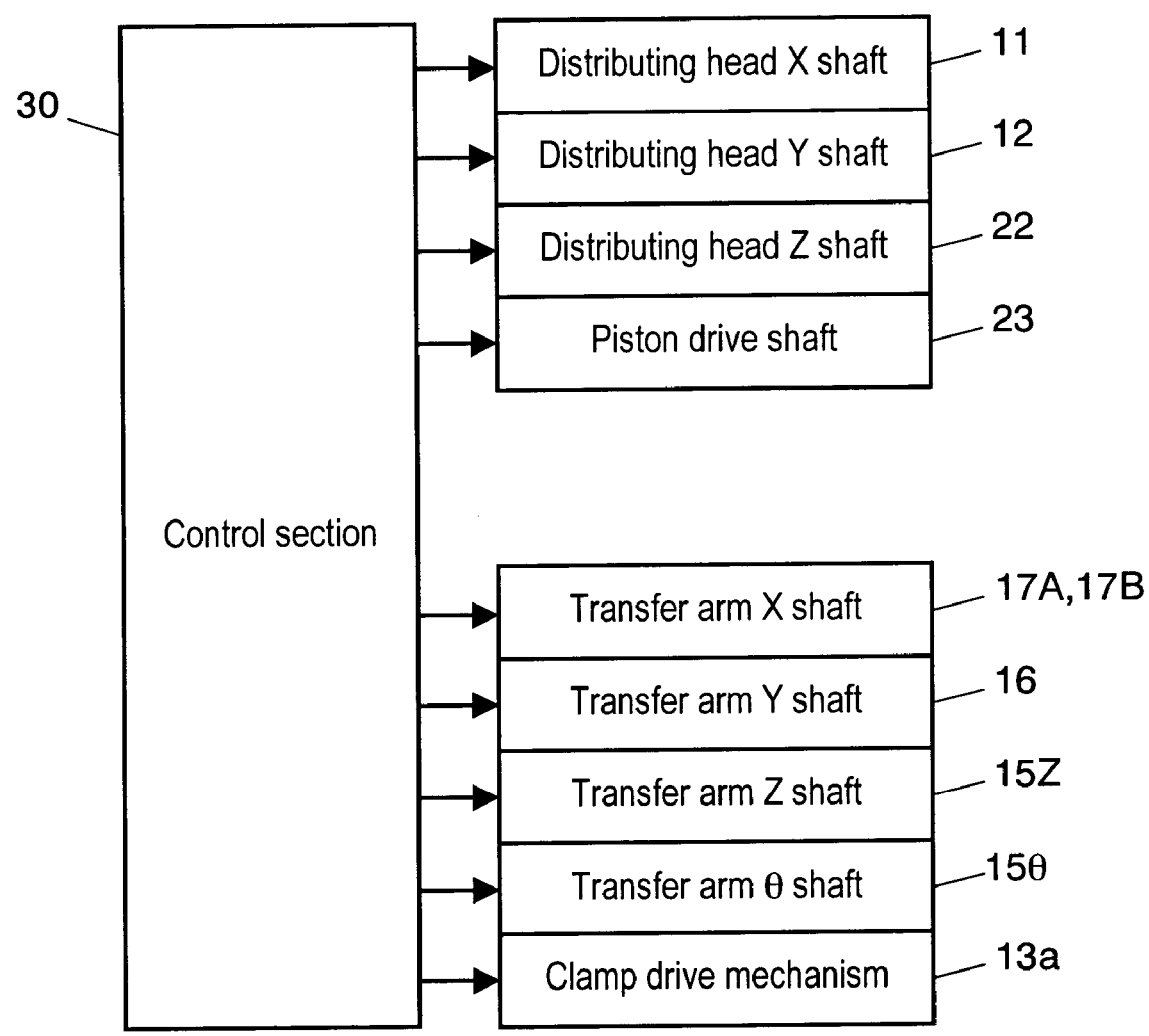
FIG. 5 is a block diagram showing the configuration of a control system of the distribution apparatus in the exemplary embodiment 1 of the present invention.
Figure 6:
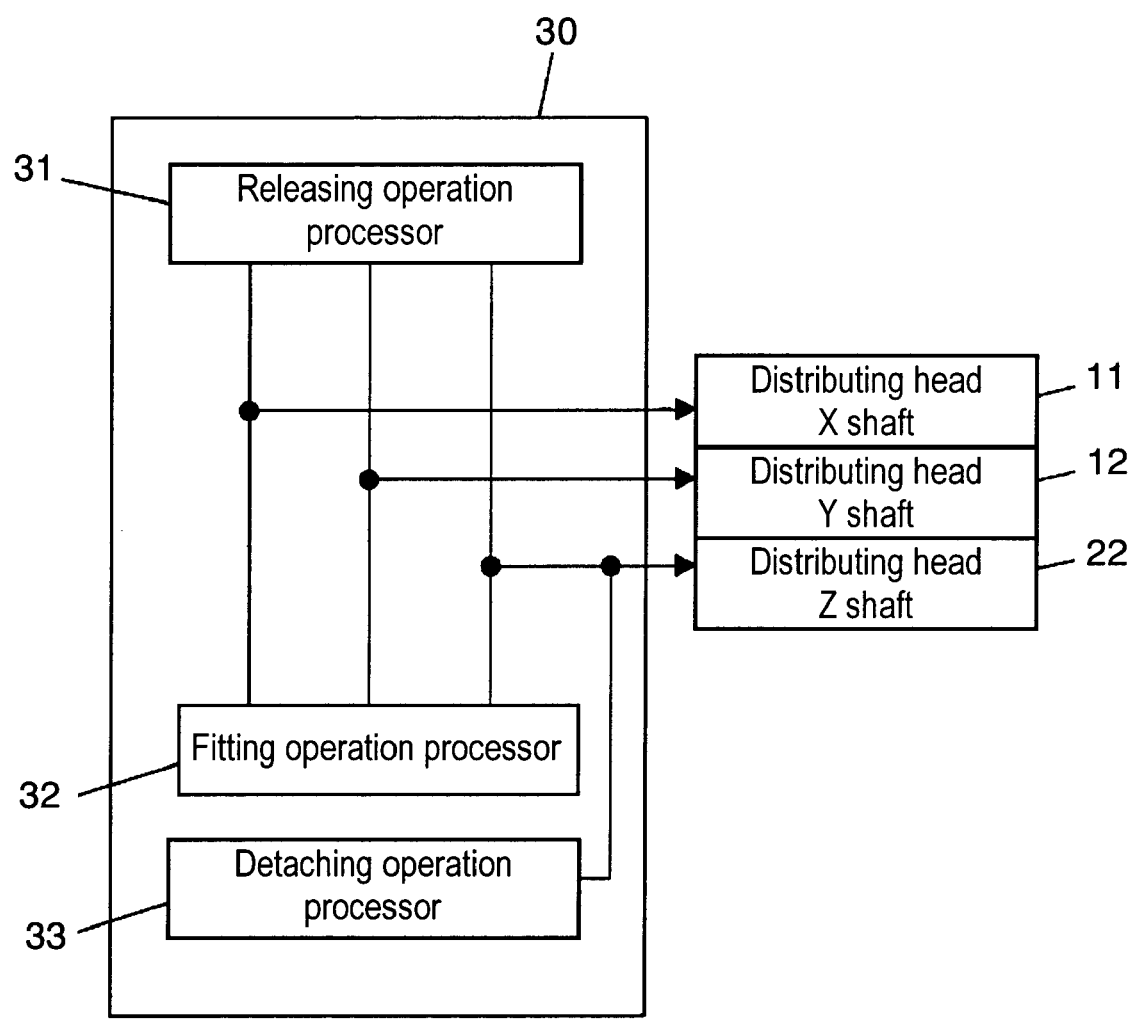
FIG. 6 is a functional block diagram showing the distribution tip detaching function of the distribution apparatus in the exemplary embodiment 1 of the present invention.

FIG. 1 is a perspective view of a distribution apparatus in the exemplary embodiment 1 of the present invention. FIG. 2 is a partly perspective view of the distribution apparatus in the exemplary embodiment 1 of the present invention. FIG. 3 is a partly perspective view of a distributing head of the distribution apparatus in the exemplary embodiment 1 of the present invention. FIG. 4 is a sectional view of the distributing head of the distribution apparatus in the exemplary embodiment 1 of the present invention. FIG. 5 is a block diagram showing the configuration of a control system of the distribution apparatus in the exemplary embodiment 1 of the present invention. FIG. 6 is a functional block diagram showing the distribution tip detaching function of the distribution apparatus in the exemplary embodiment 1 of the present invention. FIG. 6, FIG. 7, FIG. 8, FIG. 9 and FIG. 10 are the explanatory diagrams of the distribution tip detaching operation in the exemplary embodiment 1 of the present invention.

Firstly, the whole structure of the distribution apparatus is described with reference to FIG. 1. In FIG. 1, the top surface of base 1 is distributing area 1a where the distributing operation is performed. Distributing head 10 is horizontally movably arranged above the distributing area 1a by means of distributing head X shaft 11 and distributing head Y shaft 12. In the distributing area 1a, there are provided tip attaching stage 2, tip detaching stage 3, cooling stage 4, and plate mounting stage 5. As the distributing head 10 moves on each of the stages, distribution tips 7 detachably fitted to the bottom ends of nozzles 18 (see FIG. 3, FIG. 4, FIG. 8, FIG. 9) suck in the liquid and discharge it into a container, thereby executing the distributing operation.

Tip rack 6 for storing unused distribution tips 7 is mounted on the tip attaching stage 2. With the distributing head 10 moved to above the tip attaching stage 2, up-and-down moving section 10a (see FIG. 2, FIG, 4) is operated, and thereby, new distribution tips 7 are attached to nozzles 18 disposed at the bottom end of the up-and-down moving section 10a.

The tip detaching stage 3 is a stage for detaching the distribution tips 7 attached to the distributing head 10 from the distributing head 10. As shown in FIG. 2, the distributing head 10 with used distribution tips 7 attached thereto is moved to above the tip detaching stage 3, where the distributing head 10 is operated to execute the specified tip detaching operation, and thereby, the distribution tips 7 are detached from the distributing head 10 and collected into ejection port 3a.

The cooling stage 4 is a stage for mounting reservoir tank 8 containing the liquid to be distributed, which is provided with cooling function to keep the liquid at a predetermined temperature during the distributing operation. The distributing head 10 with distribution tips 7 attached thereto is moved to above the cooling stage 4, then the up-and-down moving section 10a of the distributing head 10 is moved down to insert the distribution tips 7 into the reservoir tank 8 and to suck up the liquid, and thereby, the distribution tips 7 are able to such in the predetermined amount of the liquid.

The plate mounting stage 5 is a stage for mounting micro-titer plate 9 that is a container into which the liquid is distributed. The distributing head 10 into with the liquid sucked in by the distribution tips 7 at the cooling stage 4 is lowered against the micro-titer plate 9 subjected to distributing which is disposed at the plate mounting stage 5, then the chemical solution is discharged from the distribution tips 7, and thereby, the liquid is distributed into each well of the micro-titer plate 9.

Above the distributing area 1a is arranged transfer arm 13. The transfer arm 13 is furnished with two clamp claws 14 which clamp the object to be transferred, holding it from both sides, such as the tip rack 6, reservoir tank 8, and micro-titer plate 9. The clamp claw 14 is driven by clamp drive mechanism 13a.

The transfer arm 13 can be horizontally moved by transfer arm X shaft 17A, 17B, and transfer arm Y shaft 16. Further, the transfer arm 13 can be vertically moved and axially rotated in the θ direction by transfer arm Zθ shaft 15. Thus, in the above distributing operation, the tip rack 6, reservoir tank 8 and micro-titer plate 9 can be automatically brought and taken with respect to each stage in the distributing area 1a and moved within the distributing area 1a.

Next, the structure of the distributing head 10 and the operation for attaching and detaching the distribution tips 7 to and from the distributing head 10 will be described with reference to FIG. 2, FIG. 3 and FIG. 4. As shown in FIG. 4, the distributing head 10 is internally furnished with the up-and-down moving section 10a which is moved up and down by distributing head Z shaft 22. The distributing head Z shaft 22 is configured in that belt 28 is set over pulleys 27A, 27B respectively connected with the output shaft of motor 26 and feed screw 25. When the motor 26 is driven, the up-and-down moving section 10a moves up and down along guide shaft 24.

At the bottom end of the up-and-down moving section 10a, there are provided nozzles 18 extending downwardly in lattice-work arrangement. Each of the nozzles 18 is detachably fitted with distribution tip 7. The up-and-down moving section 10a is internally furnished with a piston drive mechanism (not shown) for liquid suction and discharge, and by driving the piston drive mechanism, it is possible to suck up the liquid into the distribution tips 7 fitted in the nozzles 18 and to discharge the sucked-up liquid.

The distribution tips 7 are attached to the nozzles 18 with detaching plate 20 disposed between the bottom face of the up-and-down moving section 10a and the distribution tips 7 as shown in FIG. 2 and FIG. 4. As shown in FIG. 3, the detaching plate 20 is provided with openings 20a being larger in diameter than outer diameter of the nozzle 18 in accordance with the arrangement of the nozzles 18, and the nozzles 18 can be set through the openings 20a. The detaching plate 20 is made from magnetic plate material such as steel and is held to the bottom face of the up-and-down moving section 10a by means of magnet 19 installed in the up-and-down moving section 10a. The magnet 19 is a holding means which makes the distributing head 10 hold the detaching plate 20 with the nozzles 18 set through the openings 20a. As a holding means, besides the method of using the magnetic force of magnet, it is also preferable to use a mechanical holding means which holds the detaching plate 20 with a mechanical force.

The size of the opening 20a is smaller in diameter than outer diameter of the distribution tip 7, and with the distribution tips 7 fitted in the nozzles 18, the detaching plate 20 is moved off from the bottom of the up-and-down moving section 10a, and thereby, the distribution tips 7 can be forcibly separated by the detaching plate 20 from the nozzles 18. To separate the detaching plate 20 from the up-and-down moving section 10a, the stopping portions 20b extended sideways from two opposing sides of the detaching plate 20 are stopped by the stop portion described in the following.

As shown in FIG. 2 and FIG. 4, the tip detaching stage 3 is provided with ejection port 3a being rectangular in shape for collecting used tips, and stop members 21 are erected at the edges of two opposing sides of the ejection port 3a. The stop member 21 is provided with fitting portion 21a formed by partially cutting the stop member 21 in accordance with the position of the stopping portion 20b of the detaching plate 20. The fitting portion 21a has a hooked shape with stop portion 21b which stops thereunder the stopping portion 20b fitted into the fitting portion 21a. That is, the tip detaching stage 3 is provided with the stop member 21 having stop portion 21b which stops the stopping portion 20b of the detaching plate 20.

The configuration of a control system of the distribution apparatus is described in the following with reference to FIG. 5. In FIG. 5, control section 30 serves to control the functional elements of the moving mechanism of the distributing head 10, that is, each element of distributing head X shaft 11, distributing head Y shaft 12, distributing head Z shaft 22, and piston drive shaft 23. Also, the control section 30 serves to control the functional elements of transfer arm 13, that is, each element of transfer arm X shaft 17A, 17B, transfer arm Y shaft 16, transfer arm Z shaft 15Z, transfer arm θ shaft 15θ, and clamp drive mechanism 13a.

Next, the distribution tip detaching function of the distributing head 10 and the method of detaching the distribution tips by using the function will be described with reference to the function block diagram of FIG. 6, and FIG. 7 to FIG. 10. The distribution tip detaching function is such a function that the distribution tips 7 already used at the tip detaching stage 3 are automatically detached from the nozzles 18 after completion of a series of distributing operations executed by the distributing head 10.

As shown in FIG. 6, the distribution tip detaching function is executed as the distributing head X shaft 11, distributing head Y shaft 12 and distributing head Z shaft 22 are controlled by the control section 30. Three operations such as fitting operation, detaching operation, and releasing operation included in the distribution tip detaching operation are respectively executed by fitting operation processor 32, detaching operation processor 33, and releasing operation processor 31.

Figure 7:
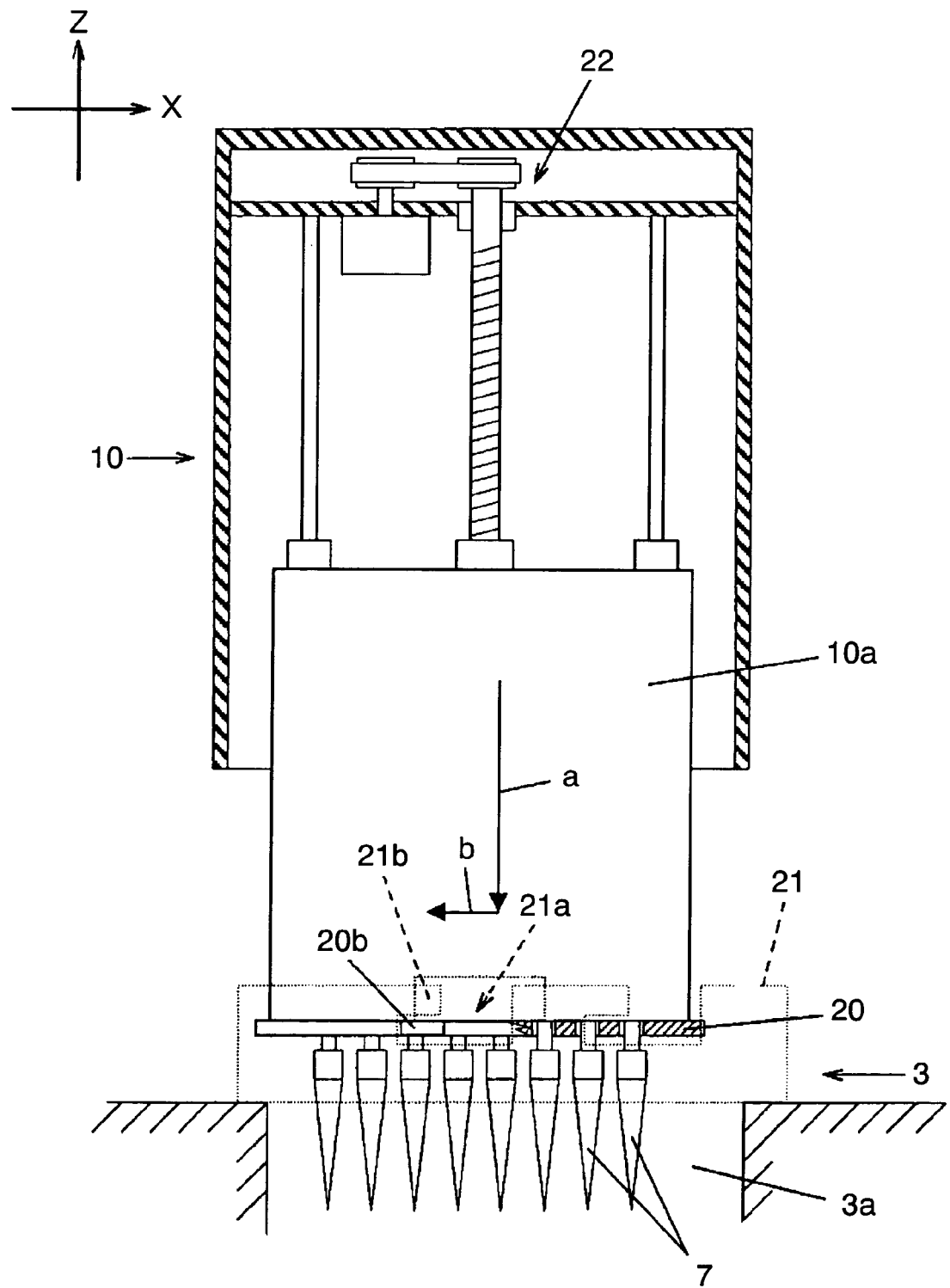
FIG. 7 is an explanatory diagram of the distribution tip detaching operation in the exemplary embodiment 1 of the present invention.

First, the fitting operation executed as the distributing head X shaft 11, distributing head Y shaft 12, and distributing head Z shaft 22 are controlled by the fitting operation processor 32 will be described with reference to FIG. 7. In FIG. 7, the distributing head 10 is moved to the tip detaching stage 3, and the stopping portion 20b of the detaching plate 20 is fitted in the fitting portion 21a of the stop member 21. In this fitting operation, the stopping portion 20b is first moved to above the opening end of the fitting portion 21a by means of the distributing head X shaft 11 and distributing head Y shaft 12, and subsequently, the stopping portion 20b is lowered into the fitting portion 21a (arrow "a") by means of the distributing head Z shaft 22. After that, the distributing head 10 is moved by the distributing head X shaft 11 in the X direction, and the stopping portion 20b is moved to underneath the stop portion 21b (arrow "b"). In this way, the stopping portion 20b is fitted in the fitting portion 21a.

Figure 8:
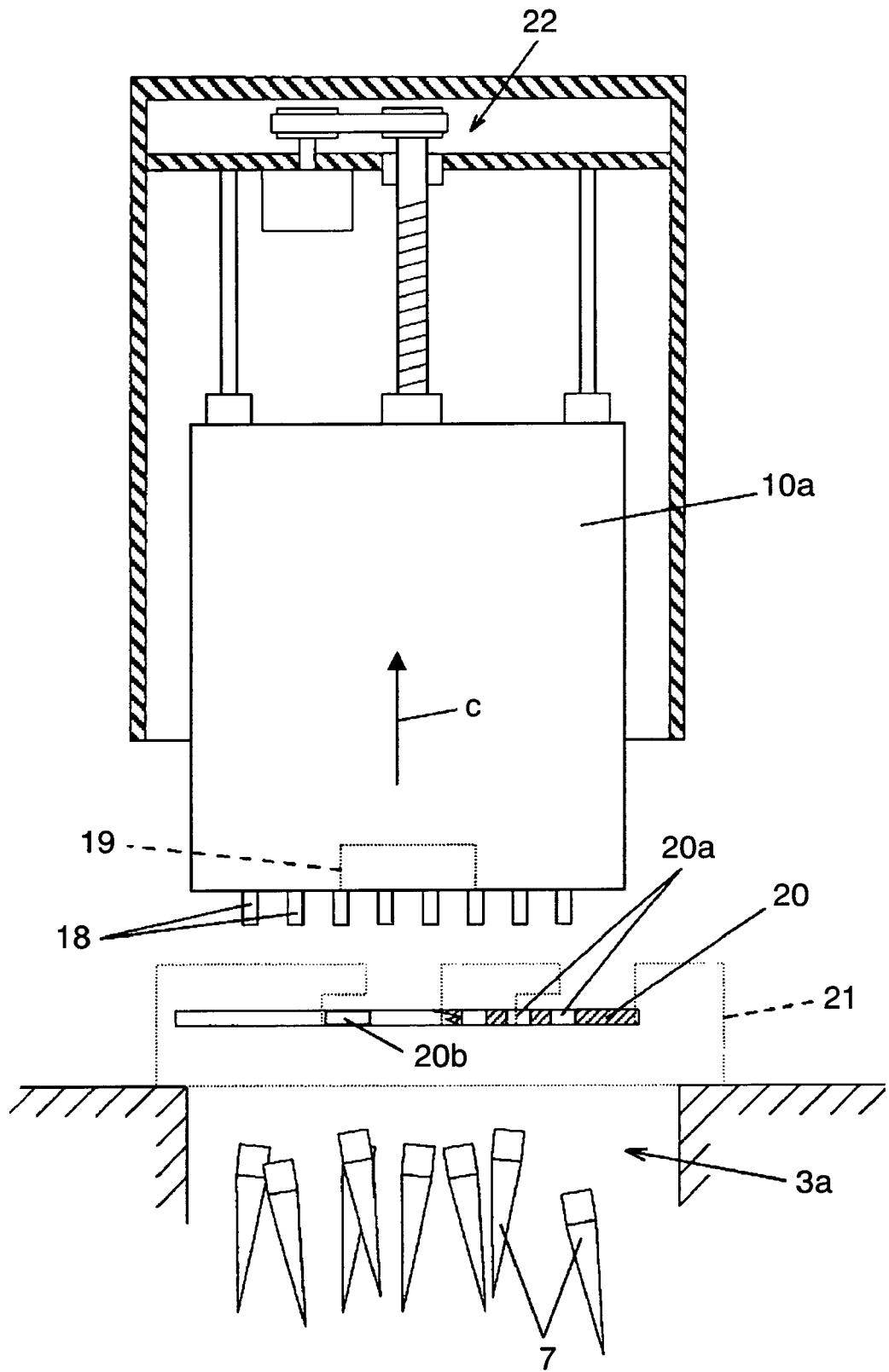
FIG. 8 is an explanatory diagram of the distribution tip detaching operation in the exemplary embodiment 1 of the present invention.

Next, the detaching operation executed as the distributing head Z shaft 22 is controlled by the detaching operation processor 33 will be described with reference to FIG. 8. In FIG. 8, the up-and-down moving section 10a is moved up (arrow "c") by the distributing head Z shaft 22 from the fitted state shown in FIG. 7. When the up-and-down moving section 10a is moved up, it tends to move up the distribution tips 7 fitted in the nozzles 18 and the detaching plate 20 together, but the detaching plate 20 is prevented from moving up because the stopping portion 20b is stopped by the stop portion 21b. Also, the distribution tip 7 is unable to move up because it is larger in outer diameter than the size of the opening 20a.

Accordingly, in the upward movement of the up-and-down moving section 10a in the above detaching operation, only the nozzle 18 moves up. And the detaching plate 20 is released from a state of being held by the magnet 19 and remains being held by the stop member 21, while the distribution tip 7 moves off from the bottom end of the nozzle 18 and drops into the ejection port 3a. In the above configuration, the distributing head Z shaft 22 serves as a distributing head moving means which moves the distributing head 10 relatively against the tip detaching stage 3. And the distributing head moving means serves as a distribution tip detaching means for detaching the distribution tip 7 from the nozzle 18 by means of the detaching plate 20, which moves the stop member 21 and the distributing head 10 relatively in a direction of vertically moving apart with the stopping portion 20b stopped by the stop portion 21b.

That is, in the above distribution apparatus, the distribution tip detaching method is such that the detaching plate 20 provided with the openings 20a beving larger in diameter than outer diameter of the nozzle 18 and smaller in diameter than outer diameter of the distribution tip 7 which are disposed in accordance with the arrangement of the nozzles 18 is held to the distributing head 10 with the nozzles 18 set through the openings 20a. And in the tip detaching operation, while the stopping portion 20b disposed at the detaching plate 20 is stopped by the stop portion 21b of the stop member 21 disposed at the tip detaching stage 3, the distributing head 10 is moved up against the tip detaching stage 3. In this way, the distributing head 10 and the stop member 21 are relatively moved in a direction of vertically moving apart, and the distribution tip 7 is detached by the detaching plate 20 from the bottom end of the nozzle 18.

Figure 9:
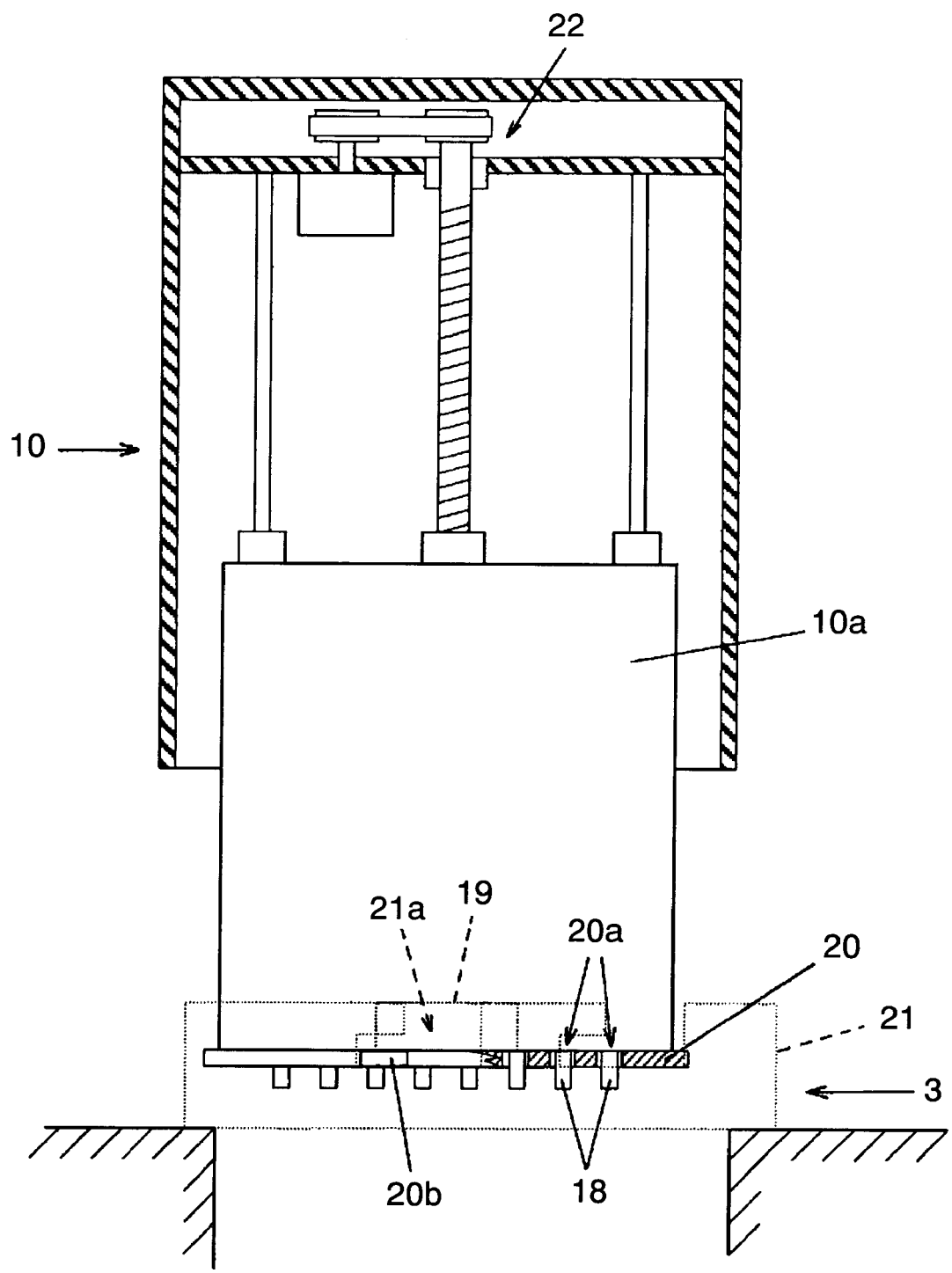
FIG. 9 is an explanatory diagram of the distribution tip detaching operation in the exemplary embodiment 1 of the present invention.

Next, the releasing operation executed as the distributing head X shaft 11, distributing head Y shaft 12, and distributing head Z shaft 22 are controlled by the releasing operation processor 31 will be described with reference to FIG. 9 and FIG. 10. In FIG. 9, the up-and-down moving section 10a is moved down, from the detached state of the distribution tips 7 shown in FIG. 8, to set the nozzles 18 through the openings 20a, and the detaching plate 20 is again held to the bottom end of the up-and-down section 10a by means of the magnet 19.

Figure 10:
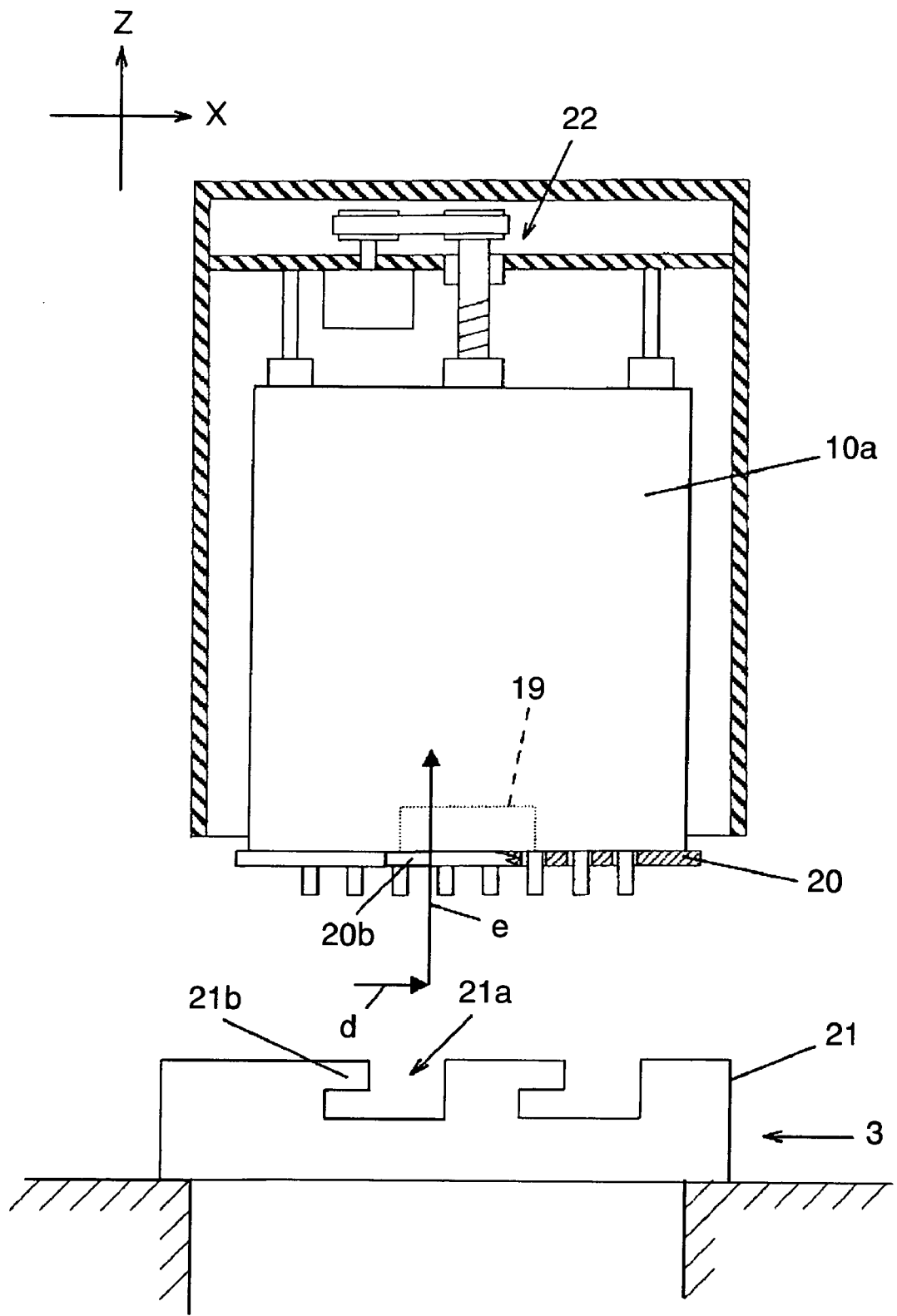
FIG. 10 is an explanatory diagram of the distribution tip detaching operation in the exemplary embodiment 1 of the present invention.

After that, the releasing operation shown in FIG. 10 is performed. First, the distributing head 10 is moved by the distributing head X shaft 11 in the X direction (arrow "d"), and the stopping portion 20b is detached from underneath the stop portion 21b. Subsequently, the up-and-down moving section 10a is moved up (arrow "e") by the distributing head Z shaft 22, then the stopping portion 20b is released from the stop portion 21a. In this way, the detaching plate 20 is released, and then, distribution tips 7 can be newly attached to the distributing head 10.

Exemplary Embodiment 2

Figure 11:
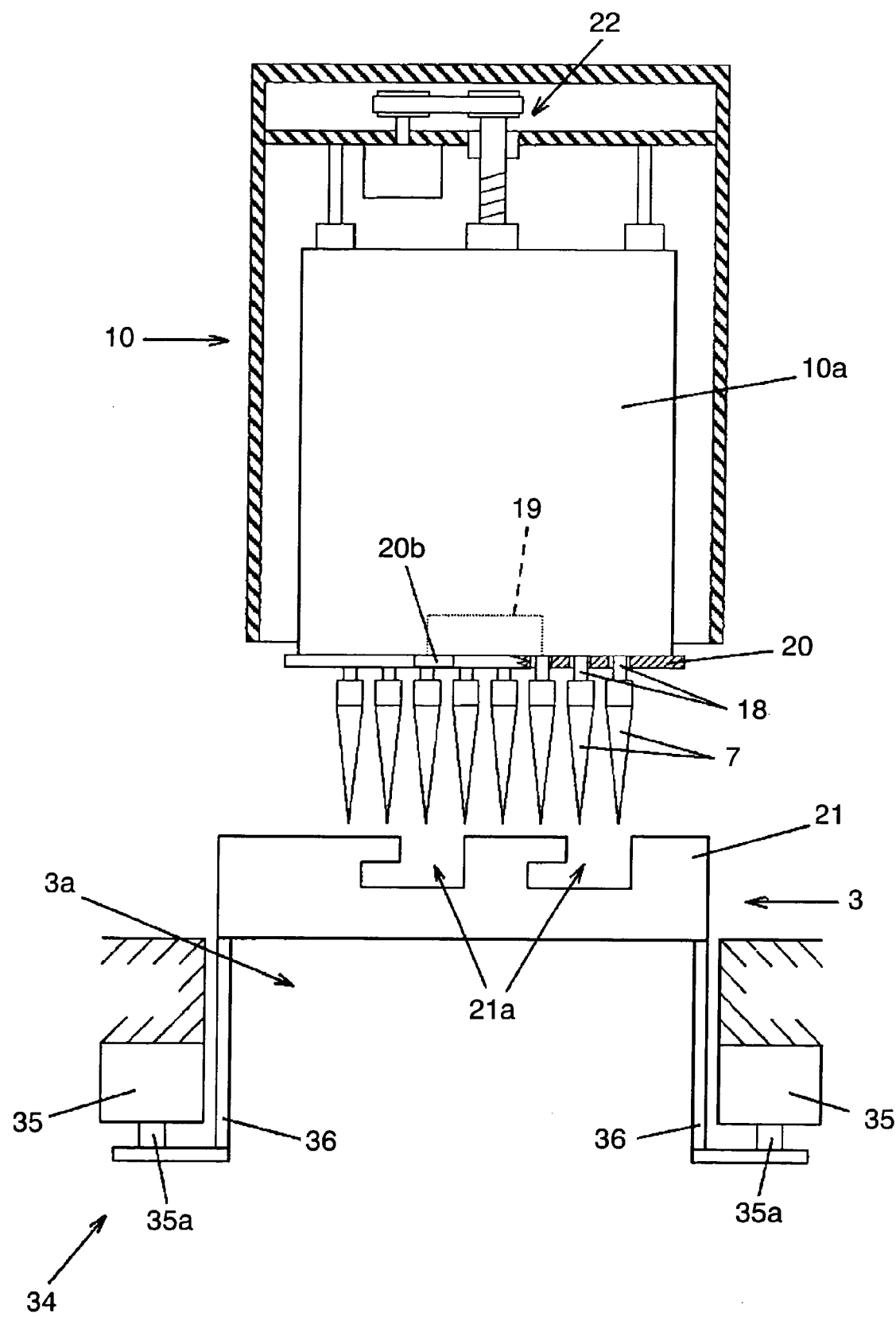
FIG. 11 is a partly sectional view of a distributing head and tip detaching stage of a distribution apparatus in the exemplary embodiment 2 of the present invention.
Figure 12:
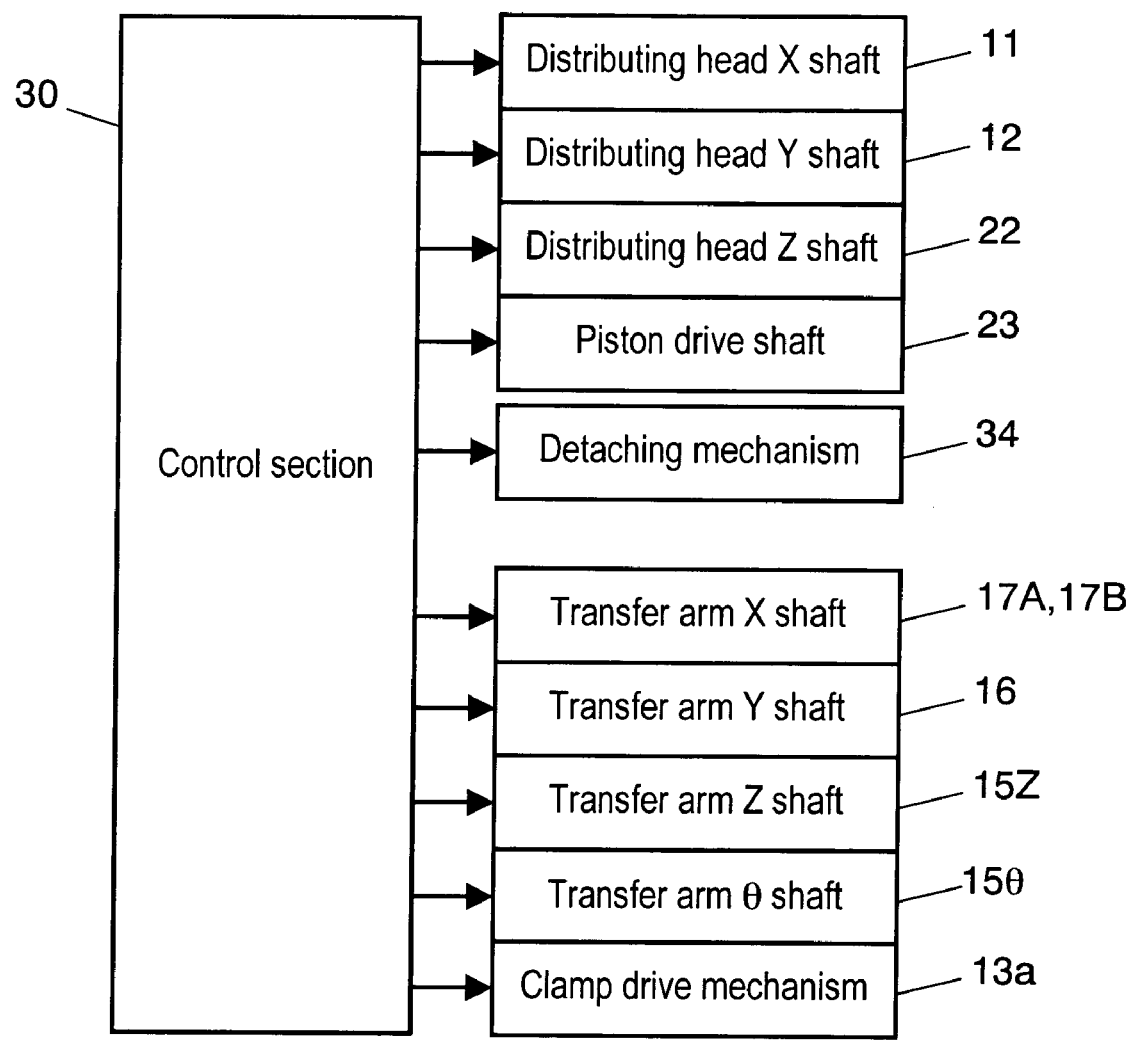
FIG. 12 is a block diagram showing the configuration of a control system of the distribution apparatus in the exemplary embodiment 2 of the present invention.
Figure 13:
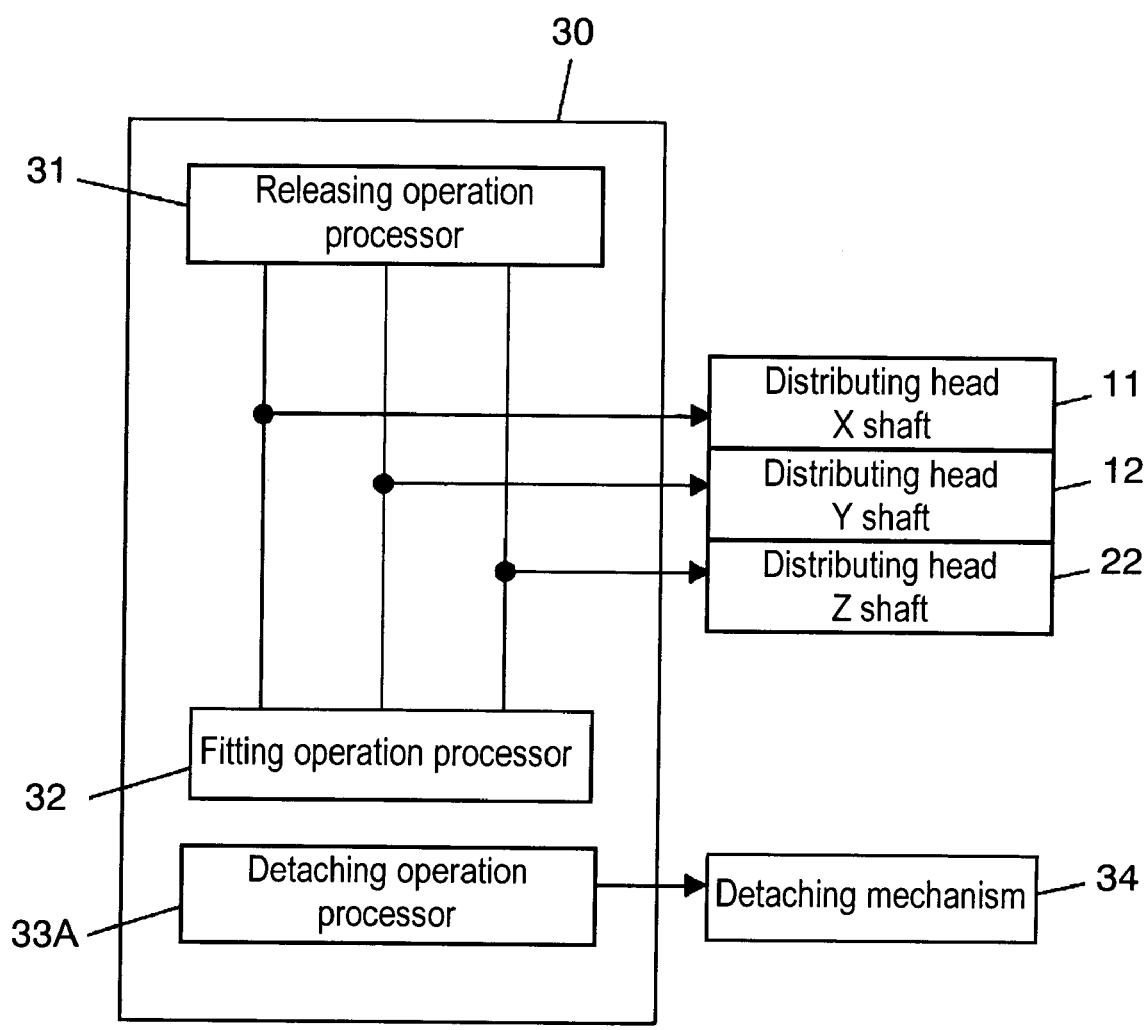
FIG. 13 is a functional block diagram showing the distribution tip detaching function of the distribution apparatus in the exemplary embodiment 2 of the present invention.
Figure 14:
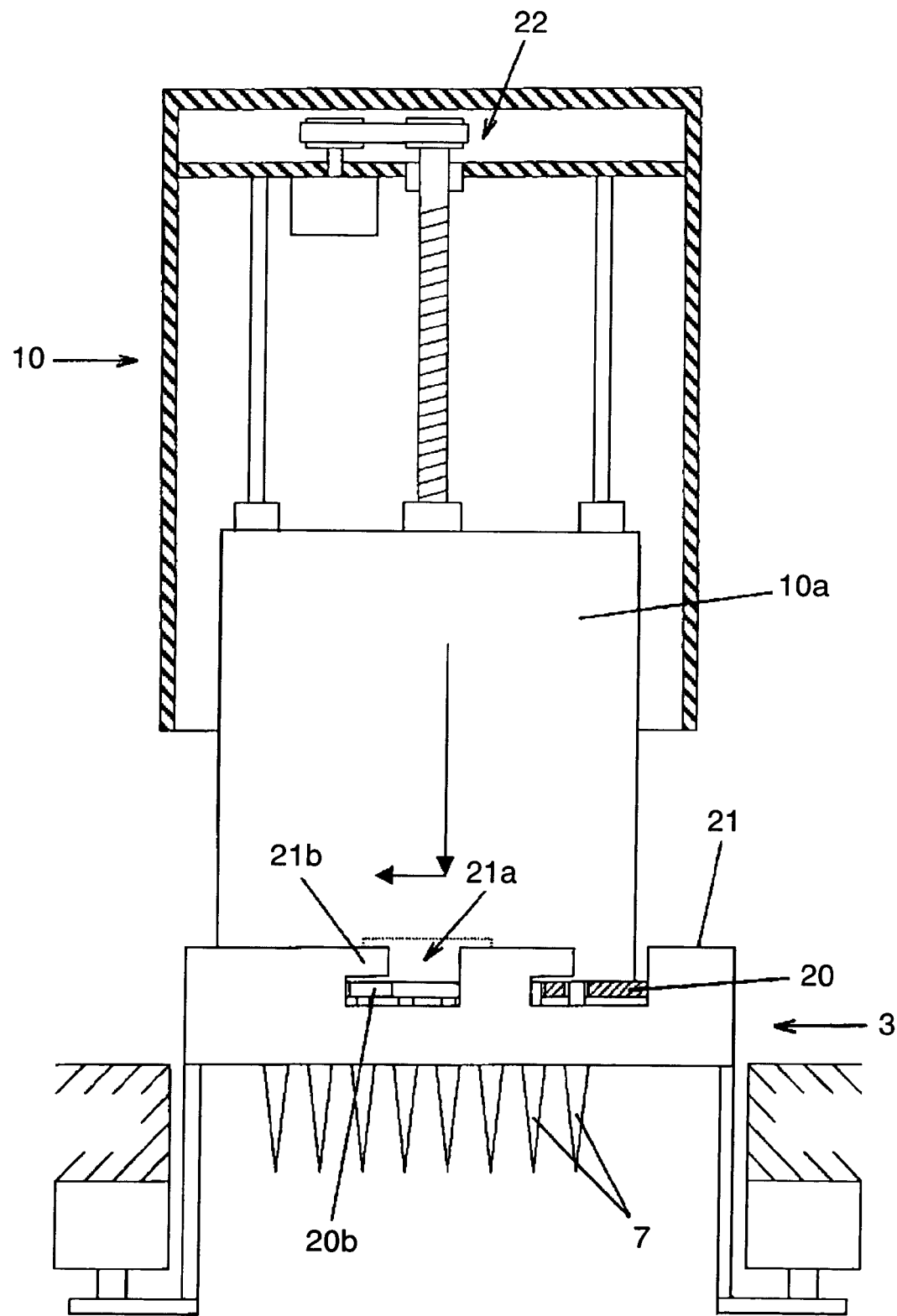
FIG. 14 is an explanatory diagram of the distribution tip detaching operation in the exemplary embodiment 2 of the present invention.
Figure 15:
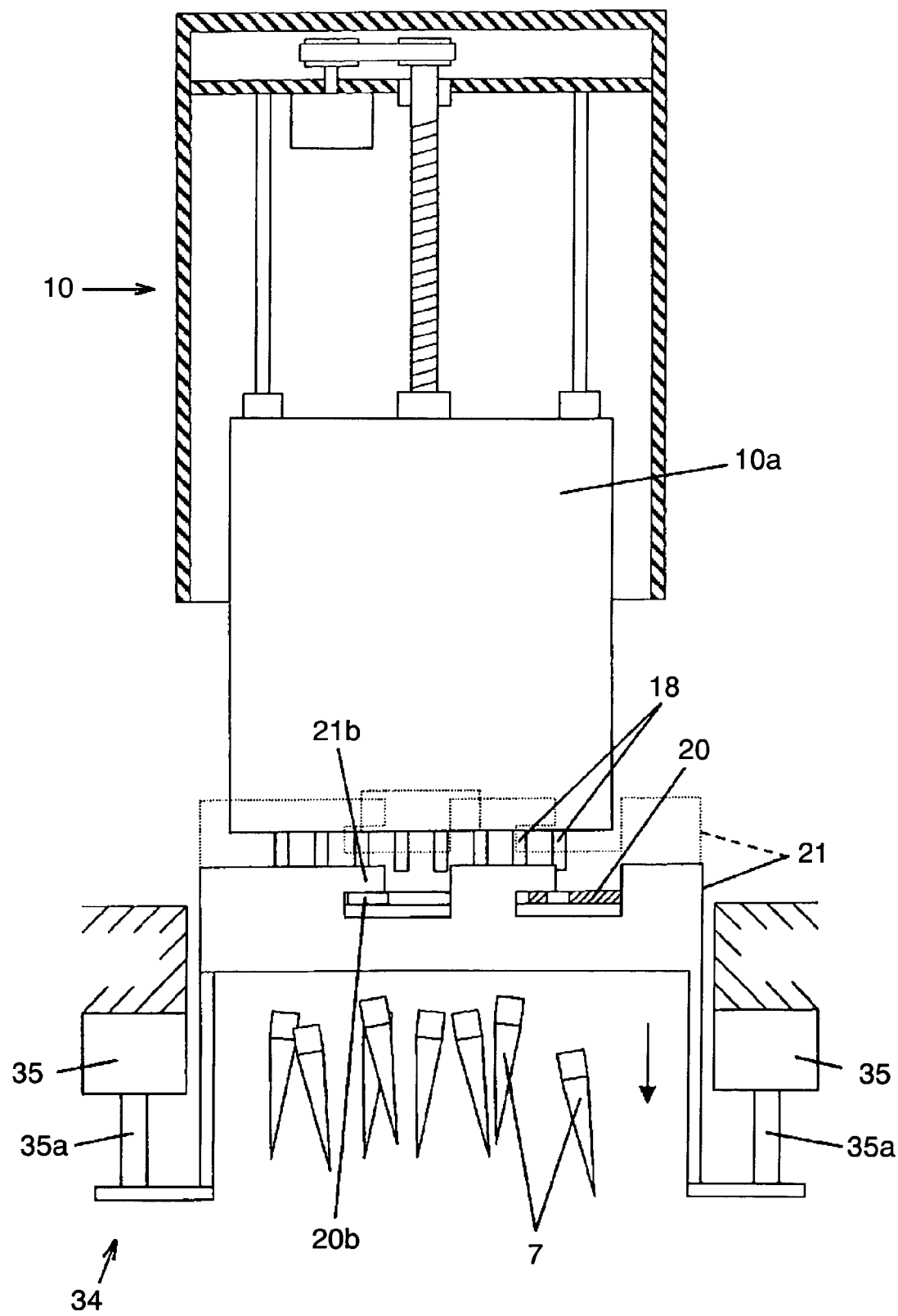
FIG. 15 is an explanatory diagram of the distribution tip detaching operation in the exemplary embodiment 2 of the present invention.

FIG. 11 is a partly sectional view of a distributing head and tip detaching stage of a distribution apparatus in the exemplary embodiment 2 of the present invention. FIG. 12 is a block diagram showing the configuration of a control system of the distribution apparatus in the exemplary embodiment 2 of the present invention. FIG. 13 is a functional block diagram showing the distribution tip detaching function of the distribution apparatus in the exemplary embodiment 2 of the present invention. FIG. 14 and FIG. 15 are the explanatory diagrams of the distribution tip detaching operation in the exemplary embodiment 2 of the present invention.

The exemplary embodiment 2 is configured in that the stop member 21 is moved down instead of moving up the distributing head 10 in the tip detaching operation for detaching the distribution tips 7 by using similar detaching plate 20 from the distributing head 10 having a similar configuration as in the exemplary embodiment 1.

In FIG. 11, the tip detaching stage 3 is furnished with ejection port 3a and stop member 21 the same as in the exemplary embodiment 1. And in the present exemplary embodiment 2, the tip detaching stage 3 is provided with detaching mechanism 34 which detaches the distribution tips 7 by means of the detaching plate 20 by lowering the stop member 21. The detaching mechanism 34 is configured in that the stop member 21 is connected to the rod 35a of cylinder 35 via connecting member 36, and the stop member 21 is moved up and down by protruding and retreating the rod 35a of the cylinder 35. The cylinder 35 serves as a stop member up-and-down moving means which moves up and down the stop member 21.

FIG. 12 shows the configuration of a control system of the distribution apparatus, having the detaching mechanism 34 to be controlled by the control section 30 in addition to the configuration shown in FIG. 5. FIG. 13 shows the distribution tip detaching function, where the functions of releasing operation processor 31 and fitting operation processor 32 are same as in the exemplary embodiment 1. And the detaching operation processing is executed as the detaching mechanism 34 is controlled by the detaching operation processor 33A.

FIG. 14 shows the fitting operation executed as the distributing head X shaft 11, distributing head Y shaft 12, and distributing head Z shaft 22 are controlled by the fitting operation processor 32 the same as in FIG. 7. Here, the stopping portion 20b of the detaching plate 20 is moved to underneath the stop portion 21b of the stop member 21 as a result of fitting operation the same as in FIG. 7.

FIG. 15 shows the detaching operation executed as the detaching mechanism 34 is controlled by the detaching operation processor 33A. That is, the rod 35a of the cylinder 35 is protruded, from the fitted state shown in FIG. 14, and the stop member 21 is lowered against the distributing head 10. Due to the lowering operation, the detaching plate 20 fitted in the stop member 21 is released from a state of being held by the magnet 19 and is also lowered as the stopping portion 20b is pushed down by the stop portion 21b. Thus, the distribution tips 7 are detached from the bottom ends of the nozzles 18. In the above configuration, the cylinder 35 being a stop member up-and-down moving means serves as a distribution tip detaching means which detaches the distribution tips 7 from the nozzles 18 by means of the detaching plate 20.

As described in the exemplary embodiments 1 and 2, the distribution tip detaching method in the distribution apparatus of the present invention is such that the detaching plate 20 configured as described above is held to the distributing head 10 and, in the tip detaching operation, the detaching plate 20 is relatively moved in a direction of vertically moving apart against the distributing head 10 by using the stop member 21. In this way, the distribution tips 7 are detached from the nozzles 18 all together only by a simple operation. Moreover, it is not necessary to provide the distributing head with any special driving means for moving up and down the detaching plate 20 against the distributing head 10. Accordingly, in the distribution tip detaching operation to be executed very frequently, the distribution tip detaching operation can be automated by using a simple mechanism and it becomes possible to enhance the efficiency of the distributing operation.

According to the present invention, the detaching plate provided with openings being larger in diameter than outer diameter of the nozzle and being smaller in diameter than outer diameter than the distribution tip which are disposed in accordance with the arrangement of the nozzles is held to the distributing head with the nozzles set through the openings, and the stopping portion of the detaching plate is stopped by the stop portion of the stop member disposed at the tip detaching stage, while the distributing head and the stop member are relatively moved in a direction of vertically moving apart so as to detach the distribution tip from the bottom end of the nozzle, and thereby, the distribution tip detaching operation can be automatically performed by a simple mechanism.

What is claimed is:

1. A distribution apparatus which sucks in a liquid by distribution tips detachably fitted to the bottom ends of nozzles disposed on a distributing head and discharges the liquid into a container, comprising:
   a distributing head including a plurality of nozzles;
   a detaching plate having a stopping portion and provided with openings, which are larger in diameter than outer diameters of the nozzles and smaller in diameter than outer diameters of the distribution tips, disposed in accordance with an arrangement of the nozzles;
   a holding means which serves to make the distributing head hold said detaching plate with the nozzles set through the openings;
   a tip detaching stage provided with a stop member having a stop portion to stop the stopping portion; and
   a distribution tip detaching means for detaching the distribution tips from the nozzles by means of said detaching plate by moving the stop member and the distributing head relatively in a direction of vertically moving apart with the stopping portion stopped by the stop portion.

2. The distribution apparatus of claim 1, wherein said distribution tip detaching means comprises a distributing head moving means for moving the distributing head relatively against said tip detaching stage.

3. The distribution apparatus of claim 1, wherein said distribution tip detaching means comprises a stop member up-and-down moving means for moving the stop member up and down.

4. A method for detaching distribution tips in a distribution apparatus, the method comprising:
   providing a distributing head including a plurality of nozzles with distribution tips fitted on said nozzles, said distribution apparatus being arranged to suck in a liquid by distribution tips detachably fitted to the bottom ends of the nozzles disposed on the distributing head;
   providing a detaching plate having openings which are larger in diameter than outer diameters of the nozzles and smaller in diameter than outer diameters of the distribution tips disposed in accordance with an arrangement of the nozzles;
   holding the detaching plate to the distributing head with the nozzles set through the openings;

stopping a stopping portion of the detaching plate by a stop portion of a stop member disposed at a tip detaching stage;

with the stopping portion of the detaching plate stopped by the stop portion of the stop member, relatively moving the distributing head and the stop member to move vertically apart such that the distribution tips are detached from the bottom ends of the nozzles.

5. The method for detaching distribution tips in a distribution apparatus of claim 4, wherein the relatively moving the distributing head and the stop member includes moving the distributing head up against the tip detaching stage, such that the distribution tips are detached from the bottom ends of the nozzles by means of the detaching plate.

6. The method for detaching distribution tips in a distribution apparatus of claim 4, wherein the relatively moving the distributing head and the stop member includes lowering the stop member against the distributing head, such that the distribution tips are detached from the bottom ends of the nozzles by means of the detaching plate.

* * * * *

UNITED STATES PATENT AND TRADEMARK OFFICE
CERTIFICATE OF CORRECTION

PATENT NO.        : 7,189,369 B2
APPLICATION NO.   : 10/658412
DATED             : March 13, 2007
INVENTOR(S)       : Akira Higuchi Page 1 of 1

It is certified that error appears in the above-identified patent and that said Letters Patent is hereby corrected as shown below:

IN THE CLAIMS

1. Claim 4 at column 8, line 59, please change "having openings which" to --having openings, which--.

2. Claim 4 at column 9, line 7, please change "vertically apart such" to --vertically apart, such--.

3. Claim 5 at column 9, line 10, please change "the relatively moving the distributing head" to --the relative moving of the distributing head--.

4. Claim 6 at column 10, lines 6-7, please change "the relatively moving the distributing head" to --the relative moving of the distributing head--.

Signed and Sealed this

Eighteenth Day of September, 2007

JON W. DUDAS
*Director of the United States Patent and Trademark Office*